US011337928B2

(12) United States Patent
Bacchi

(10) Patent No.: US 11,337,928 B2
(45) Date of Patent: May 24, 2022

(54) METHOD AND APPARATUS FOR MAKING A TABLET OF POWDERED PRODUCTS FOR ESPRESSO BEVERAGE EXTRACTION

(71) Applicant: Andrea Bacchi, Correggio (IT)

(72) Inventor: Andrea Bacchi, Correggio (IT)

(*) Notice: Subject to any disclaimer, the term of this patent is extended or adjusted under 35 U.S.C. 154(b) by 0 days.

(21) Appl. No.: 16/113,797

(22) Filed: Aug. 27, 2018

(65) Prior Publication Data

US 2019/0000105 A1 Jan. 3, 2019

Related U.S. Application Data

(63) Continuation of application No. 14/434,040, filed as application No. PCT/IB2013/059580 on Oct. 23, 2013, now Pat. No. 10,092,019.

(30) Foreign Application Priority Data

Oct. 24, 2012 (SM) .................. SM-A-201200046

(51) Int. Cl.
*A23F 5/12* (2006.01)
*A61K 9/20* (2006.01)
(Continued)

(52) U.S. Cl.
CPC .............. *A61K 9/2095* (2013.01); *A23F 5/12* (2013.01); *A23L 5/15* (2016.08); *A23P 10/20* (2016.08);
(Continued)

(58) Field of Classification Search
CPC .... A23F 5/12; A23F 5/125; A23F 5/38; A23P 10/20; A23P 10/28; A23P 10/25;
(Continued)

(56) References Cited

U.S. PATENT DOCUMENTS 1,723,069 A * 8/1929 Peter ................... A23F 5/125
206/499
1,951,357 A 2/1931 Hall
(Continued)

FOREIGN PATENT DOCUMENTS

EP 1956921 8/2008
FR 1029940 12/1950
(Continued)

OTHER PUBLICATIONS

Pneumatictips NPL, published Sep. 26, 2012, https://www.pneumatictips.com/what-are-pneumatic-cylinders/#:~:text=Pneumatic%20actuators%20are%20mechanical%20devices,load%20along%20a%20linear%20path.&text=Double%2Dacting%20cylinders%20have%20an,receives%20the%20high%20pressure%20air. (Year: 2012).*

*Primary Examiner* — Drew E Becker
*Assistant Examiner* — Bryan Kim
(74) *Attorney, Agent, or Firm* — Themis Law

(57) ABSTRACT

A method of making a tablet for hot espresso beverage extraction includes the steps of grinding a brewable product to obtain a powder having a substantially uniform particle size, dosing a predetermined amount of the ground product powder, moistening the powdered product dose, homogenizing the moistened mixture to obtain a powdered product with a substantially uniform moisture content, forming the powdered product dose to obtain a disk-shaped or prismatic tablet, and supplying an amount of energy to the tablet to obtain a substantially compact and integral item. The step of supplying energy is carried out by irradiating the tablet with an electromagnetic wave beam to overheat and partially bake and/or sinter the particles of the powdered product and impart a relatively compact and self-supporting construction to the finished tablet. The electromagnetic wave irradiation (Continued)

step is carried out at the end of the forming step while continuously compressing the dose.

3 Claims, 3 Drawing Sheets

(51) Int. Cl.
    *A23P 10/28*     (2016.01)
    *A23P 10/20*     (2016.01)
    *A23L 5/10*     (2016.01)
    *A47J 31/44*     (2006.01)
    *B30B 11/00*     (2006.01)

(52) U.S. Cl.
    CPC ............ *A23P 10/28* (2016.08); *A47J 31/4403* (2013.01); *A61K 9/20* (2013.01); *A23F 5/125* (2013.01); *A23V 2002/00* (2013.01); *B30B 11/00* (2013.01)

(58) Field of Classification Search
    CPC ......... A23P 30/10; A61K 9/20; A61K 9/2095; A23L 5/15; B30B 11/00; B30B 11/004; B30B 11/007; B30B 11/008; B30B 11/02; B30B 11/022; B30B 11/025; B30B 11/027; B30B 11/04; B30B 11/08; B30B 11/14

See application file for complete search history.

(56) References Cited

U.S. PATENT DOCUMENTS

| | | | | |
|---|---|---|---|---|
| 2,495,429 A * | 1/1950 | Spencer | ............. | A23L 5/15 219/728 |
| 3,121,635 A * | 2/1964 | Eldred | ............. | A23F 5/385 426/242 |
| 3,293,041 A * | 12/1966 | Miller | ............. | A23F 3/32 426/454 |
| 3,293,042 A * | 12/1966 | Eitzen | ............. | A23F 5/125 426/77 |
| 4,246,462 A * | 1/1981 | Meisel | ............. | A21B 1/48 219/697 |
| 4,394,395 A | 7/1983 | Rostagno et al. | | |
| 5,082,681 A * | 1/1992 | Barlow | ............. | A01J 25/12 425/311 |
| 5,202,139 A * | 4/1993 | Gaon | ............. | H05B 6/782 426/242 |
| 5,235,150 A * | 8/1993 | Buske | ............. | A47J 37/015 219/722 |
| 5,818,014 A * | 10/1998 | Smith | ............. | G07F 9/105 219/679 |
| 5,846,584 A * | 12/1998 | Capodieci | ............. | A21C 11/00 426/238 |
| 5,914,309 A | 6/1999 | Ulbl et al. | | |
| 6,210,625 B1 * | 4/2001 | Matsushita | ............. | B01J 2/006 264/109 |
| 6,563,097 B2 * | 5/2003 | Taino | ............. | H05B 6/6402 219/711 |
| 6,982,094 B2 * | 1/2006 | Sowden | ............. | A23G 3/04 424/400 |
| 8,088,322 B2 * | 1/2012 | Arkenau-Maric | ............. | A61P 25/18 264/443 |
| 8,313,768 B2 * | 11/2012 | Kriksunov | ............. | A61J 3/10 264/239 |
| 8,336,557 B2 * | 12/2012 | Kumar | ............. | A23G 3/48 131/111 |
| 8,389,036 B2 * | 3/2013 | Diolaiti | ............. | A23F 3/32 426/238 |
| 8,511,159 B2 * | 8/2013 | Kloter | ............. | G01F 23/284 324/637 |
| 8,858,210 B2 * | 10/2014 | Szymczak | ............. | A61K 9/0056 264/449 |
| 9,445,971 B2 * | 9/2016 | Anderson | ............. | A61J 3/00 |
| 2003/0127455 A1 | 7/2003 | Poss | | |
| 2010/0183773 A1 * | 7/2010 | Malone | ............. | B65D 21/086 426/107 |
| 2011/0070286 A1 | 3/2011 | Hugerth et al. | | |
| 2011/0071184 A1 | 3/2011 | Bunick et al. | | |
| 2011/0287168 A1 * | 11/2011 | Buzsaky | ............. | A61K 9/1694 427/2.18 |
| 2012/0121789 A1 * | 5/2012 | Briend | ............. | A23F 5/38 426/590 |
| 2014/0234947 A1 * | 8/2014 | Jones | ............. | C07G 1/00 435/277 |

FOREIGN PATENT DOCUMENTS

| | | |
|---|---|---|
| IT | 1213385 | 12/1989 |
| WO | 0127426 | 4/2001 |
| WO | WO2013001052 A1 | 1/2013 |

* cited by examiner

METHOD AND APPARATUS FOR MAKING A TABLET OF POWDERED PRODUCTS FOR ESPRESSO BEVERAGE EXTRACTION

FIELD OF THE INVENTION

The present invention generally finds application in the food industry and particularly relates to a method and arrangement for making a tablet of powdered products for espresso beverage extraction.

BACKGROUND OF THE INVENTION

Certain espresso beverages are known to be obtained by brewing or instantaneous extraction of flavors and active ingredients of more or less edible products, such as coffee, barley, malt, ginseng, infusions and other similar products in powder or particle form, using warm or hot water at ambient pressure or preferably at a pressure above the atmospheric pressure.

As used herein, the term espresso is intended to designate a beverage that is prepared instantaneously or for a waiting consumer.

A particular class of base products requires grinding to obtain products of various particle sizes.

A typical, non-exclusive example of such class of products is coffee, which is previously mixed, roasted and then cold-ground to obtain the classical coffee grounds that are sold in hermetically and vacuum sealed packages for home and public use.

In order to prepare an espresso coffee, a given amount of coffee grounds is loaded in a perforated container, known as filter container, whereupon the loaded grounds are compressed manually or using a special tamper.

Then, hot water is forced through the compressed grounds are at a given pressure, using a special machine.

A high-quality espresso coffee, as typically requested in bars, requires some skill and a high-cost professional machine.

For domestic preparation of high-quality espresso coffee, portions of coffee grounds have been long available, which are pre-packaged as pods made of filter paper or plastic capsules of various shapes and sizes. These items are introduced into relatively inexpensive machines, which are affordable to private consumers or small-size businesses and communities, to prepare a top-quality espresso.

Examples of these pre-packaged items are disclosed, for instance, in FR 1 029 940, U.S. Pat. No. 1,951,357, 4,394,395, IT 1 213 385.

One drawback of such prior art methods and items for preparing espresso coffee consists in the relatively high costs for manufacturing and packaging capsules or pods, which results in accordingly high sales costs for the final consumer.

A further drawback is that this known type of packaging requires the presence of enclosures made of plastic, paper, aluminum or other materials to contain the products to be filtered, which make the manufacturing process more complex and problematic.

Yet another drawback relates to environment-friendly disposal and environmental impact reduction issues, due to such enclosures, after coffee dispensing.

In an attempt to obviate the above drawbacks, a novel process has been developed for producing tablets or pastilles that does not require any kind of enclosure, but requires moistening of the tablet and application of energy thereto, in the form of vibrations, namely high-frequency ultrasonic vibrations.

Processes of this type are disclosed and claimed, for instance, in EP1956921 e WO2001/027426.

While this novel preparation method has provided a number of advantages over prior art products, such as the elimination of the plastic enclosure for coffee grounds, which considerably reduces environmental impact, it still has the drawback that vibrations are required to be transferred by contact or through an interposed medium, which increases the complexity and costs of the manufacturing process.

Furthermore, the tablet is not uniformly compacted, as ultrasonic waves are progressively attenuated as they pass through the tablet, and the tablet cannot be compacted above a given thickness limit.

SUMMARY OF THE INVENTION

The object of the present invention is to overcome the above drawbacks, by providing a method of producing a tablet of ground powdered products for hot espresso beverage extraction that is highly efficient and relatively cost-effective.

A particular object of the present invention is to provide a method as described above which avoids the use of enclosures for tablets of brewable products.

A further object is to conceive a method as described above which affords a considerable reduction of manufacturing process and equipment costs.

Yet another object is to provide a tablet for espresso beverage preparation that has a substantially integral self-supporting construction.

These and other objects, as more clearly shown hereinafter, are fulfilled by a method of making a tablet for hot espresso beverage extraction, comprising the steps of grinding a brewable product to obtain a powder having a substantially uniform particle size, dosing a predetermined amount of said ground product powder, moistening the powdered product dose, forming the dose of moistened powdered product by compression to obtain a substantially disk-shaped tablet, supplying an amount of energy to said tablet to obtain a substantially compact and integral item.

The method is characterized in that the step of supplying energy is carried out at a distance by irradiating the tablet with an electromagnetic wave beam to overheat and partially bake and/or sinter the particles of the powdered product as well as to impart a relatively compact and self-supporting construction to the tablet.

In a second aspect, the invention relates to an arrangement for making a tablet of ground powdered products for hot espresso beverage extraction, which comprises forming means having a hollow body for collecting a powdered product dose, compression means for compressing the product dose collected in said hollow body and forming a tablet having a desired shape, means for supplying energy to the tablet formed within said hollow body.

In a further aspect, the means for supplying energy comprise irradiating means for remote emission of an electromagnetic wave beam directed toward said hollow body, to overheat and partially bake and/or sinter the particles of the powdered products of the tablet as well as to impart thereto a relatively compact and self-supporting construction without requiring any outer enclosure.

Particular embodiments of the method and arrangement of the invention are described hereinafter.

BRIEF DESCRIPTION OF THE DRAWINGS

Further characteristics and advantages of the invention will be more apparent upon reading of the detailed description of a few preferred, non-exclusive embodiments of a method and apparatus for producing a tablet for hot espresso beverage extraction, which are described as non-limiting examples with the help of the annexed drawings, in which.

DETAILED DESCRIPTION OF EMBODIMENTS OF THE INVENTION

Particularly referring to the above mentioned figures, the method for producing a tablet for hot espresso beverage extraction may be advantageously used for brewable products of various types, as long as they can be actually brewed, including without limitation coffee, barley, malt, ginseng, tea, hibiscus tea, infusions and other similar products in powder or particle form.

While the method is described below with reference to a coffee tablet, it is applicable to any of the above mentioned products.

Figure 1:
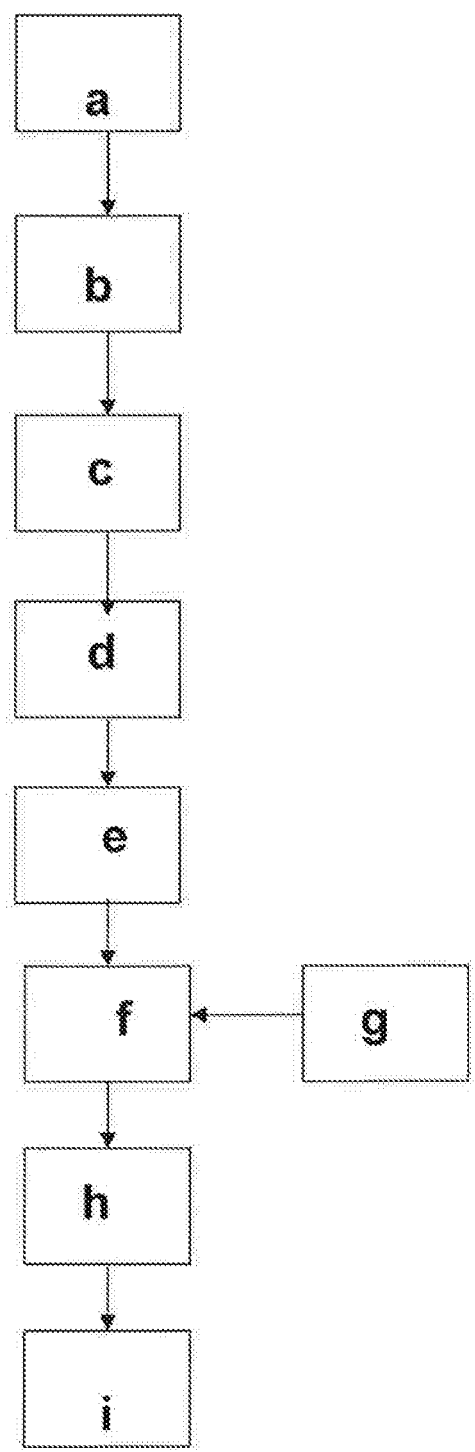
FIG. 1 is a block diagram of the inventive method.

As briefly shown in the block diagram of FIG. 1 the method comprises a previous preparation of a blend of coffee grains, after conventional roasting.

Then, the coffee blend undergoes a grinding step a) to obtain grounds having a substantially uniform particle size, herein referred to as "powered product" substantially in the dry state or with very low residual moisture content.

The powdered product will undergo a dosing step b) by special volumetric dosing or weighing units, such that a dose of a predetermined amount of product is isolated.

The product dose will undergo a moistening step c) with 2% to 20%, preferably about 10% liquid, preferably untreated water, based on the weight of dry powdered product.

Possibly, appropriate binders may be used for improving mutual adhesion of the powder particles in the later steps.

The powdered product, after addition of water and other binders, if any, will preferably undergo a homogenization step d), e.g. by stirring with a special spindle or vibration mixer, or with any other means that can provide a substantially uniform moistened mixture.

Now, the moistened and homogenized mixture undergoes a forming step e) to assume a predetermined shape.

Particularly, the forming step e) may be carried out by an apparatus as described below, which is adapted to compress the moistened mixture into an item, e.g. a disk-shaped or prismatic item, hereinafter referred to as tablet C or pastille.

Preferably, the pressure applied to the powdered product ranges from 1 bar to 5 bar, and is preferably about 2.5 bar. Conveniently, compression will be carried out by pneumatic, hydraulic or technically equivalent means.

The tablet C so formed shall be anyway adapted to be introduced into a hot water or steam coffee machine of a known type and also suitable for use in home environments.

A key step of the step is the supply d) of a given amount Q of energy, which causes heating of the previously formed tablet C, to impart a substantially compact and integral construction thereto.

A peculiar feature of the invention is that the step f) of supplying said energy is carried out by irradiating the tablet C with an electromagnetic wave beam.

Conveniently, the irradiation step starts as soon as the forming step is completed, and while continuously holding the tablet under pressure throughout the irradiation step, to stabilize the shape and structure of the tablet C.

Electromagnetic waves are known to be a form of energy that is transferred through space without requiring any interface of contact medium, whereby this step may be carried out at a distance, by simply directing the beam toward the tablet.

Tests and analyses showed that the best results are obtained by selecting an electromagnetic wave frequency in the microwave range.

Particularly the frequency of microwaves may advantageously range from 0.915 to 5.8 GHz, and preferably be about 2.45 GHz.

Microwave irradiation is conducted in a substantially constant fashion, for a predetermined time T, ranging from a few seconds to 2 minutes, and preferably less than 60 seconds.

Preferably, the electromagnetic beam has a specific power P ranging from 30 to 500 W per gram of powdered product, preferably of about 150 W per gram of powdered product.

It will be appreciated that the powdered product that forms the tablet C contains a given amount of water, whose molecules behave like electric dipoles having a given dipole moment.

Since the wavelength of microwaves is of the same order of magnitude as that of water dipoles, microwaves will cause an increase of the rotational energy of such dipoles in the mass of the tablet C, thereby almost instantaneously heating water and the surrounding product.

Since water molecules are substantially evenly distributed in the mass of the tablet, the base material of the tablet will undergo substantially uniform and "core" heating, without creating zones with differentiated hardness.

Therefore, the compressed and microwave-irradiated granular product will be somewhat "baked" and/or "sintered" in a very short time, typically a few seconds, thereby creating a self-supporting and integral structure, which is considerably porous and extractable, in the tablet.

The need is thus avoided for any outer enclosure, which would also have some barrier effect, and may limit flavor extraction from the product.

At the end of the energy supply step f), a short rest step h) may be envisaged for the tablet C, followed by a step in which the latter undergoes individual or multiple packaging i).

An arrangement that may be used for carrying out the above mentioned process comprises, in sequence, volumetric dosing or weighing units for isolating a dose of a predetermined amount of product, a special spindle, vibration mixer or any other homogenizing means for stirring the powdered product and providing a substantially uniform moistened mixture and an apparatus that may be used for carrying out the forming step e) and the electromagnetic irradiation step g).

Figure 2:
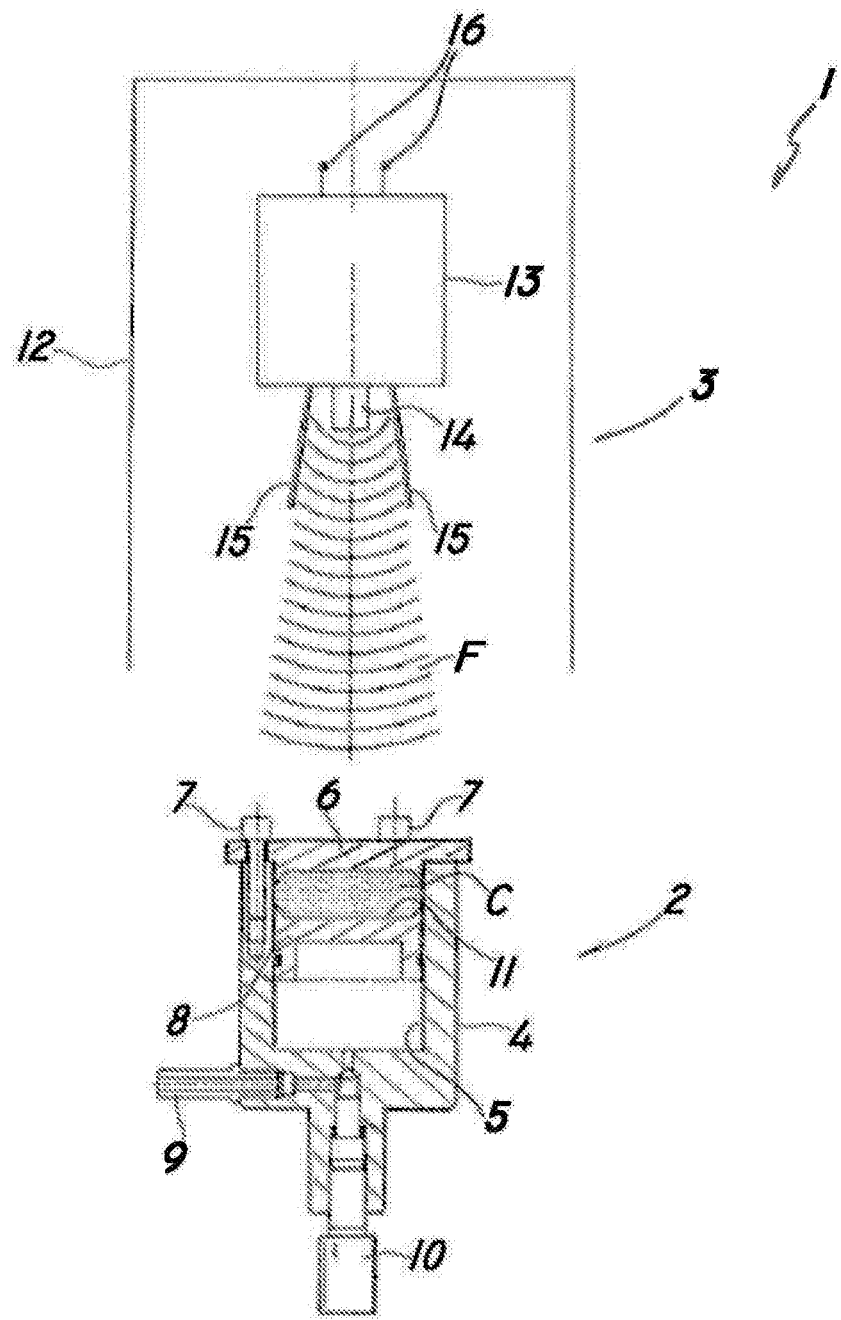
FIG. 2 is a schematic view of a first embodiment of an apparatus for carrying out certain steps of the method of FIG. 1.

FIG. 2 shows a first embodiment of an apparatus which is generally designated with numeral 1 and comprises a forming device 2 and an irradiation device 3.

The forming device 2 comprises a substantially tubular body 4 with a substantially cylindrical inner cavity 5, closed at its bottom and with a top opening designed to be closed by a cover 6 that may be removably locked by screw fastener means 7.

Both the inner cavity 5 and the closure means 6, 7 may have a configuration other than that described above, without departing from the scope of the invention.

A piston 8 is sealingly and slidably housed in the cavity 5 and may be pushed upwards by compressed air or an equivalent pressurized fluid introduced into the cavity through a lateral air duct 9.

An air exhaust valve 10 is provided in the lower portion of the tubular body 4, to remove compressed air after compression.

A compression chamber 11 is created between the top face of the piston 8 and the bottom face of the cover 6, for receiving the powdered product dose which is later compressed.

Possibly, air bleeder means, not shown, may be provided in the compression chamber, to avoid backpressures in the chamber 11 as the piston 8 rises.

The irradiation device 3 may comprise a bell-shaped shield 12 holding therein a generator 13 of electromagnetic, particularly microwave waves, e.g. a magnetron as typically used in home microwave ovens.

The generator 13 is equipped with an antenna 14 and deflection mirrors or waveguides 15, which have the purpose of directing the beam F toward the target, i.e. the forming device 2, from a distance and in contactless fashion.

As is known per se, the generator 13 receives power from a power source connected to its terminals 16 via a cable and a switch, not shown.

In operation, once the powdered product dose has been poured into the compression chamber 11, the cover 6 has been secured by the screw fastener means 7 and the valve 10 has been closed, air at an appropriate pressure is introduced, to push the piston 8 upwards, compress the powdered product dose and form the tablet C.

Immediately after complete formation of the tablet C, i.e. when the piston 8 has reached its uppermost position and has compressed the powdered product dose, the generator 13 is powered and emits the beam F to irradiate the tablet C.

Of course, for loss- or spark-free irradiation, the forming device 2 shall be entirely formed with microwave transparent materials.

Figure 3:
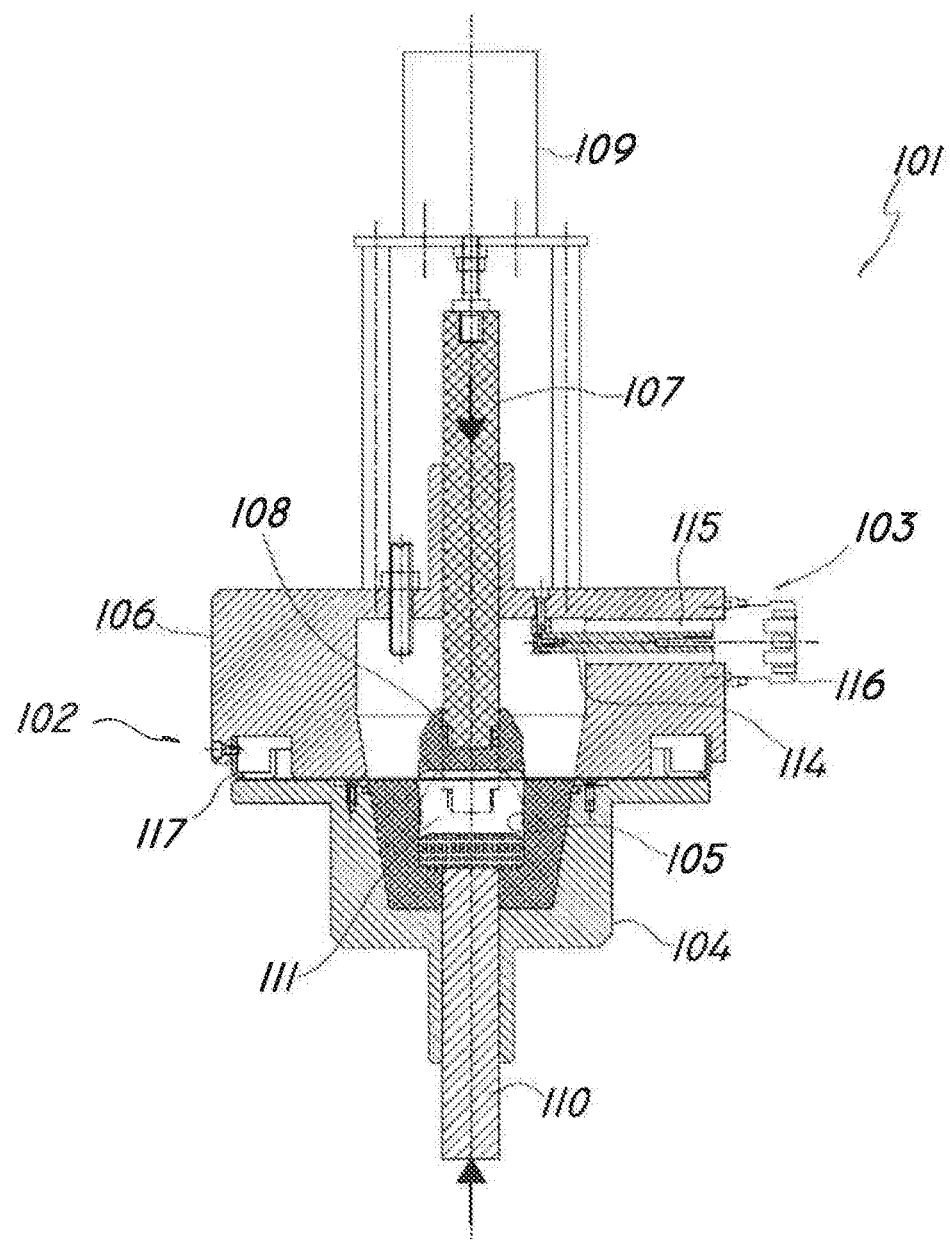
FIG. 3 is a schematic view of a variant embodiment of the apparatus of FIG. 2.

FIG. 3 shows an alternative embodiment of the apparatus of FIG. 2, referenced 101, which basically comprises a forming device 102 and an electromagnetic wave beam irradiating device 103.

Here again the forming device 102 may essentially consist of a hollow body 104 with an inner cavity 105 or a forming die adapted to receive a unit powdered product dose. For this purpose, the inner cavity 105 has a substantially cylindrical shape, or anyway a shape substantially conforming that of the tablet C to be formed.

The hollow body 104 also has an upper flange and is closed by a removable cover 106 having an upper opening for the passage of the stem 107 of a piston 108. The stem 107 is connected at its top to an actuator 109, e.g. consisting of a pneumatic or hydraulic cylinder, which is connected to a pressurized fluid source, not shown.

Possibly, a presser 110 may be provided in the lower portion of the hollow body 104, for ejecting the finished tablet C once heat treatment thereon is completed.

A variable-volume compression chamber 111 is thus formed between the inner cavity 105 and the piston 108, which is designed to compress the powdered product dose and form the tablet C.

A radiant device, generally referenced 103 is associated with the forming device 102, and comprises an electromagnetic wave beam emitting antenna 114.

The antenna 114 is at the end of a waveguide 115 having at its end a connection 116 for a coaxial cable connected to a microwave generator, e.g. a magnetron, both not shown.

Conveniently, an annular labyrinth shield 117 may be arranged along the outer peripheral edge of the cover 106, for cooperating with the upper flange of the hollow body 102 to hold the microwaves within the radiant device 103.

While the above described embodiments of the apparatus are both designed to form one tablet at a time, further embodiments may be provided of an apparatus for packaging multiple tablets at a time, which would be designed to be introduced into a mass production line.

An exemplary process of making a tablet or pastille C is briefly described below.

EXAMPLE

A typical coffee blend is used, which is instantly ground.

Then a dosed amount of 7.2 grams of coffee grounds is separated. 0.8 grams of water are added, and accurately mixed for moisture homogenization.

The dose is poured into the compression chamber 11, 111 of the forming device 2, 102. Compressed air at a pressure of about 2.6 bar is introduced into the inner cavity 5 or the pneumatic cylinder of the actuator 109 to compress the powdered product and form an approximately disk-shaped tablet C having a diameter of 40 mm and a thickness of about 9.5 mm.

Now, the microwave generator is turned on for a time T of about 10 seconds, to generate a beam F having a power of about 1000 W.

The weight of the pastille after baking is about 7.6 grams, with a total mass loss of about 0.4 grams due to partial evaporation of water and the liquid components of coffee.

The above described method and apparatus fulfill the intended objects as stated in the introduction, and particularly provide a tablet of ground powdered products for hot espresso beverage extraction having remarkable efficiency and self-support features, without using any outer enclosure and with a considerable manufacturing cost reduction.

The method and apparatus of this invention are susceptible to a number of changes or variants, within the inventive concept disclosed in the appended claims. All the details thereof may be replaced by other technically equivalent parts, and the materials may vary depending on different needs, without departure from the scope of the invention as defined in the claims.

The invention claimed is:
1. An apparatus for making a tablet for extraction of an espresso beverage using one or more ground brewable products comprising:
   a volumetric dosing or weighing unit adapted to isolate a product dose of a predetermined volume or weight of the one or more ground brewable products;
   wherein the product dose is moistened with water;
   a homogenizing device adapted to stir the product dose after moistening the one or more ground brewable products;
   a forming device comprising,
      a substantially tubular body having a substantially cylindrical inner cavity, a top opening and a removable and lockable closure body; wherein the inner cavity is configured to receive the product dose; and
      a piston sealingly, slidingly, and entirely housed in said inner cavity and actuated by a pressurized fluid to contact and compress the product dose received within said inner cavity, and to form a tablet having a predetermined shape; and an irradiating device connected to an energy supplying unit, the irradiating device being adapted to irradiate a microwave beam to the product dose within the inner cavity, wherein the irradiating device comprises a microwave generator connected to an antenna equipped with deflection mirrors or waveguides adapted to direct the microwave beam toward the inner cavity of said forming device while the piston is in a position of compression of the product dose to form the tablet, wherein said forming device, including the substantially tubular body having the substantially cylindrical inner cavity, the piston, and the removable and lockable closure body, is entirely made of microwave transparent material, and wherein the microwave beam generated by the irradiating device has a power ranging from 30 to 500 W/gram of the one or more ground brewable products.

2. The apparatus as claimed in claim 1, wherein the substantially cylindrical inner cavity has an end closed by the piston and an opposite end, said opposite end closed by the removable and lockable closure body, wherein said closure body is configured to be opened for receiving the product dose and to be closed to define a compression chamber having a shape corresponding to a shape of the tablet to be formed.

3. The apparatus as claimed in claim 2, wherein the substantially tubular body has a substantially cylindrical shape provided with an upper flange closed by the removable and lockable closure body, said closure body having an outer peripheral edge, wherein an annular labyrinth shield is arranged along the outer peripheral edge to cooperate with the flange to hold the microwaves within the forming device.

* * * * *